US009663255B2

(12) United States Patent  
Ritola

(10) Patent No.: US 9,663,255 B2  
(45) Date of Patent: May 30, 2017

(54) HINGED STRAP-BINDER

(71) Applicant: Irvin W. Ritola, Yacolt, WA (US)

(72) Inventor: Irvin W. Ritola, Yacolt, WA (US)

(*) Notice: Subject to any disclaimer, the term of this patent is extended or adjusted under 35 U.S.C. 154(b) by 979 days.

(21) Appl. No.: 13/850,545

(22) Filed: Mar. 26, 2013

(65) Prior Publication Data

US 2013/0206018 A1   Aug. 15, 2013

Related U.S. Application Data

(62) Division of application No. 12/622,091, filed on Nov. 19, 2009, now Pat. No. 8,402,887.

(60) Provisional application No. 61/117,825, filed on Nov. 25, 2008.

(51) Int. Cl.
| | |
|---|---|
| *B65B 13/02* | (2006.01) |
| *B65D 63/06* | (2006.01) |
| *B65D 63/08* | (2006.01) |
| *B65D 63/16* | (2006.01) |
| *F16L 3/233* | (2006.01) |

(52) U.S. Cl.
CPC .............. *B65B 13/02* (2013.01); *B65D 63/06* (2013.01); *B65D 63/08* (2013.01); *B65D 63/16* (2013.01); *F16L 3/233* (2013.01); *Y10T 24/47* (2015.01); *Y10T 24/4745* (2015.01)

(58) Field of Classification Search
CPC ........ B65B 13/02; B65D 63/08; B65D 63/16; B65D 63/06; F16L 3/233; A44B 11/12; A44B 11/125; A44B 11/18; A44B 11/006; A44B 11/2542; A44B 11/2538; Y10T 24/4745; Y10T 24/47; Y10T 24/4072; Y10T 24/4016

USPC ................ 100/8, 9, 29, 30, 32, 33 PB, 212; 24/265 EC, 265 R, 170, 191, 134 R, 168

See application file for complete search history.

(56) References Cited

U.S. PATENT DOCUMENTS

| | | | |
|---|---|---|---|
| 1,758,831 A | 5/1930 | Haubert | |
| 2,825,109 A * | 3/1958 | Nelson ................. | A44B 11/125 24/273 |
| 4,221,029 A | 9/1980 | Jerome | |
| 4,348,824 A | 9/1982 | Treadwell | |
| 4,714,016 A | 12/1987 | Bond | |

(Continued)

FOREIGN PATENT DOCUMENTS

| | | |
|---|---|---|
| CA | 2557638 A1 | 3/2007 |
| EP | 0826593 | 3/1998 |

(Continued)

*Primary Examiner* — Jimmy T Nguyen  
(74) *Attorney, Agent, or Firm* — Stoel Rives LLP

(57) ABSTRACT

A multi-component binding-strap fastener for binding volumetric objects with a strap tension a strap around the volumetric objects is described. The strap may engage the binding-strap fastener by bending an end of the strap to secure the strap through a plurality of apertures in the binding-strap fastener, by friction, by pressure, by any combination of the foregoing, or other suitable manner. A binding-strap fastener may lock in a closed position using a locking device, such as an over-center mechanism, a retaining clip, or a strap-engaging portion. The A binding-strap fastener has a hinge located thereon between a first end of the binding-strap fastener and a second end of the binding-strap fastener, where the axis of rotation is coincident with the hinge and the axis of rotation is located above the volumetric object.

18 Claims, 16 Drawing Sheets

SHOWN WITH STEEL BANDING

(56) References Cited

U.S. PATENT DOCUMENTS

| | | | |
|---|---|---|---|
| 4,903,348 A | 2/1990 | Broersma | |
| 5,036,864 A | 8/1991 | Yewer, Jr. | |
| 5,096,323 A | 3/1992 | Walker | |
| 5,572,771 A | 11/1996 | Kelleghan | |
| 5,632,457 A | 5/1997 | Neely, Jr. | |
| 5,689,868 A | 11/1997 | Hartmann | |
| 6,401,305 B1 | 6/2002 | Joseph | |
| 6,412,794 B1 | 7/2002 | Phillips et al. | |
| 6,431,315 B1 | 8/2002 | Lewis | |
| 6,477,747 B1 | 11/2002 | Flagg | |
| 6,683,258 B1 | 1/2004 | Tracy et al. | |
| 7,210,317 B2 | 5/2007 | Beane et al. | |
| 7,290,486 B2 | 11/2007 | Lafond | |
| 7,591,222 B2 | 9/2009 | Alain | |
| 7,634,841 B2 | 12/2009 | Profit | |
| 2006/0005360 A1 | 1/2006 | Profit | |
| 2007/0251314 A1 | 11/2007 | Molenaar et al. | |
| 2008/0185489 A1 | 8/2008 | Ehrgott | |
| 2008/0209702 A1* | 9/2008 | Van Dine | A43C 11/14 24/68 SK |

FOREIGN PATENT DOCUMENTS

| | | | | |
|---|---|---|---|---|
| GB | 137029 | | 11/1920 | |
| GB | 2122296 A | * | 1/1984 | ........... A44B 11/125 |
| GB | 2218459 A | * | 11/1989 | ........... A44B 11/125 |
| GB | EP 0413521 A1 | * | 2/1991 | ........... A44B 11/125 |
| WO | WO 98/54051 | | 12/1998 | |

* cited by examiner

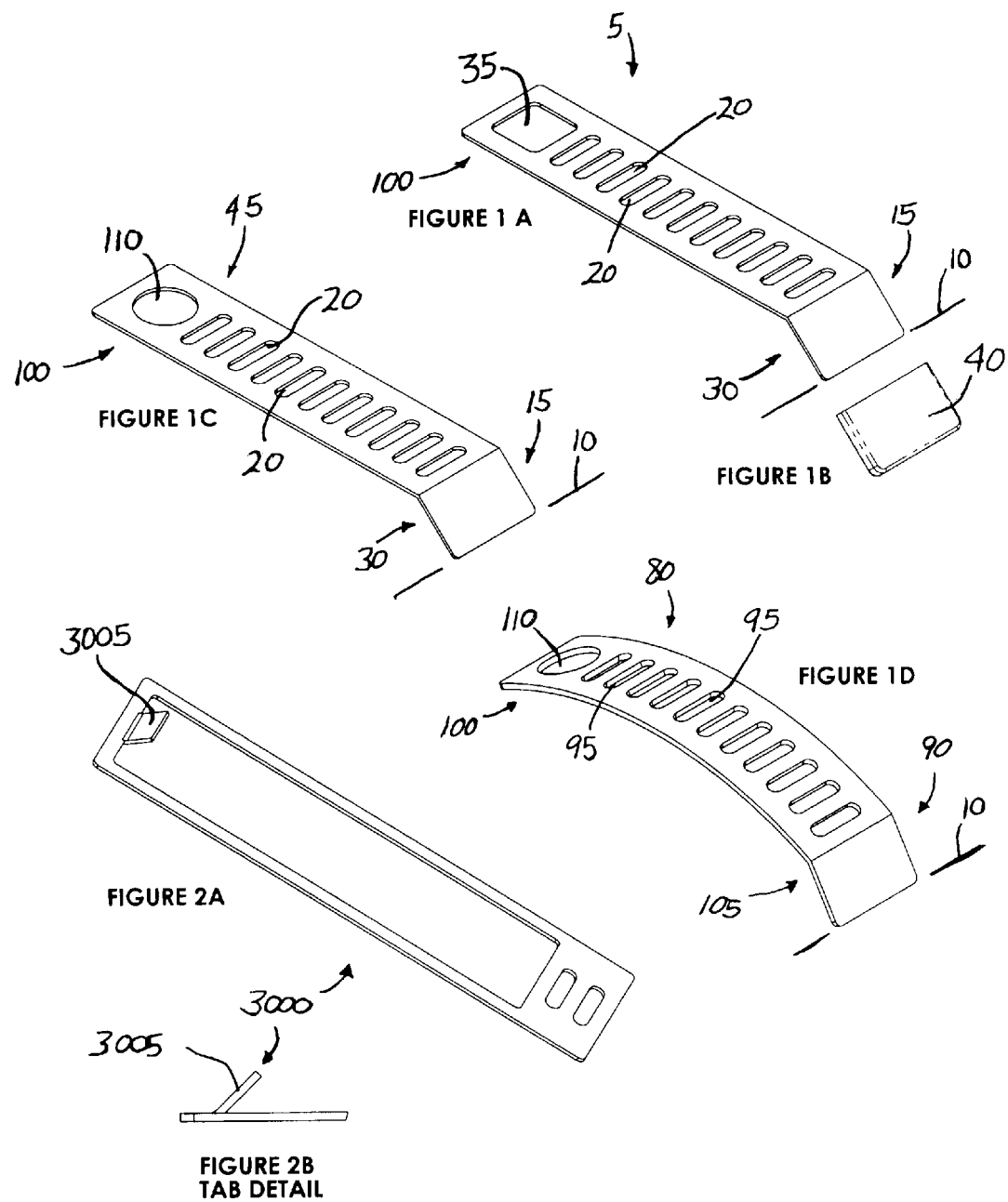

END VIEW

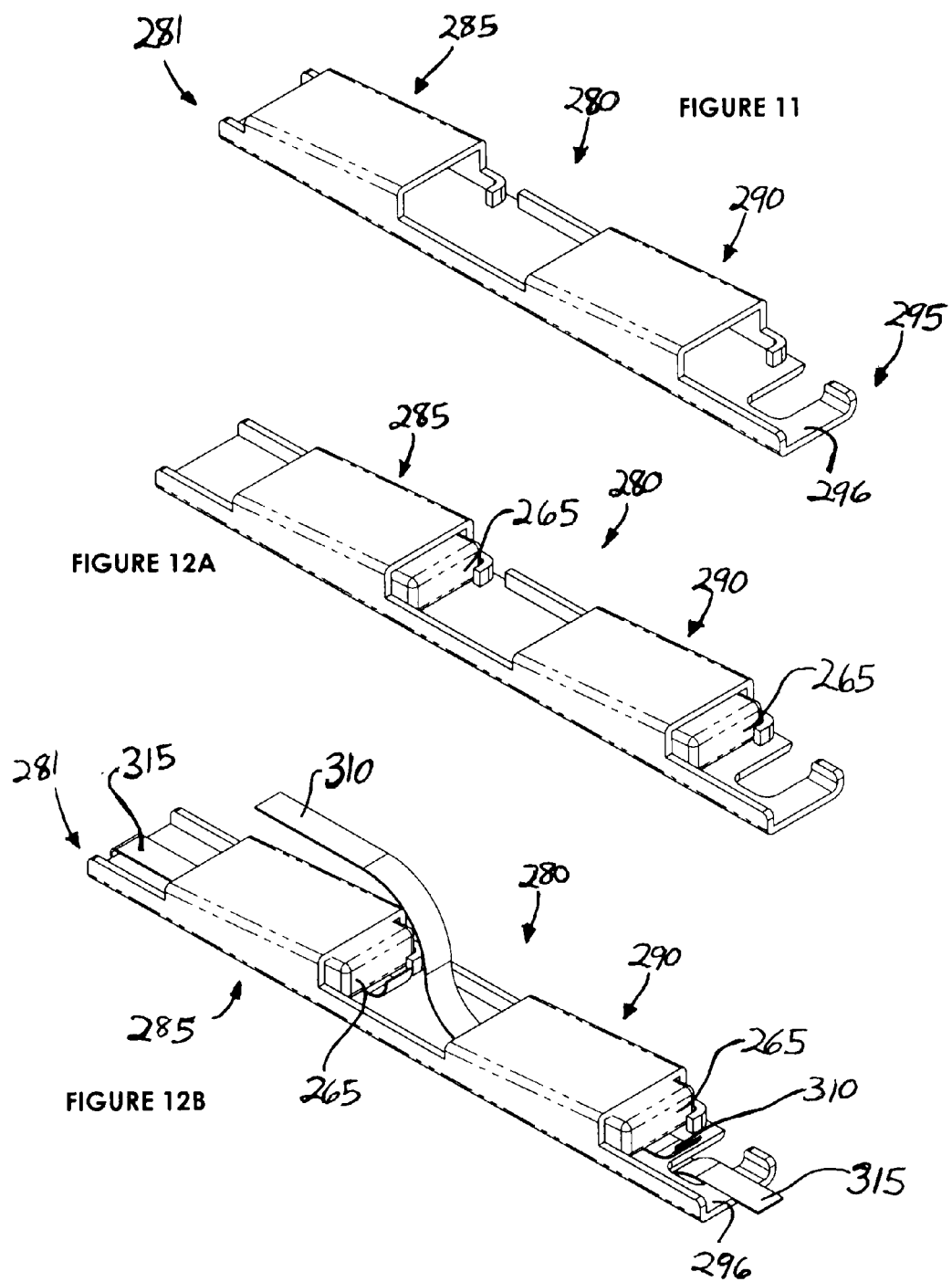

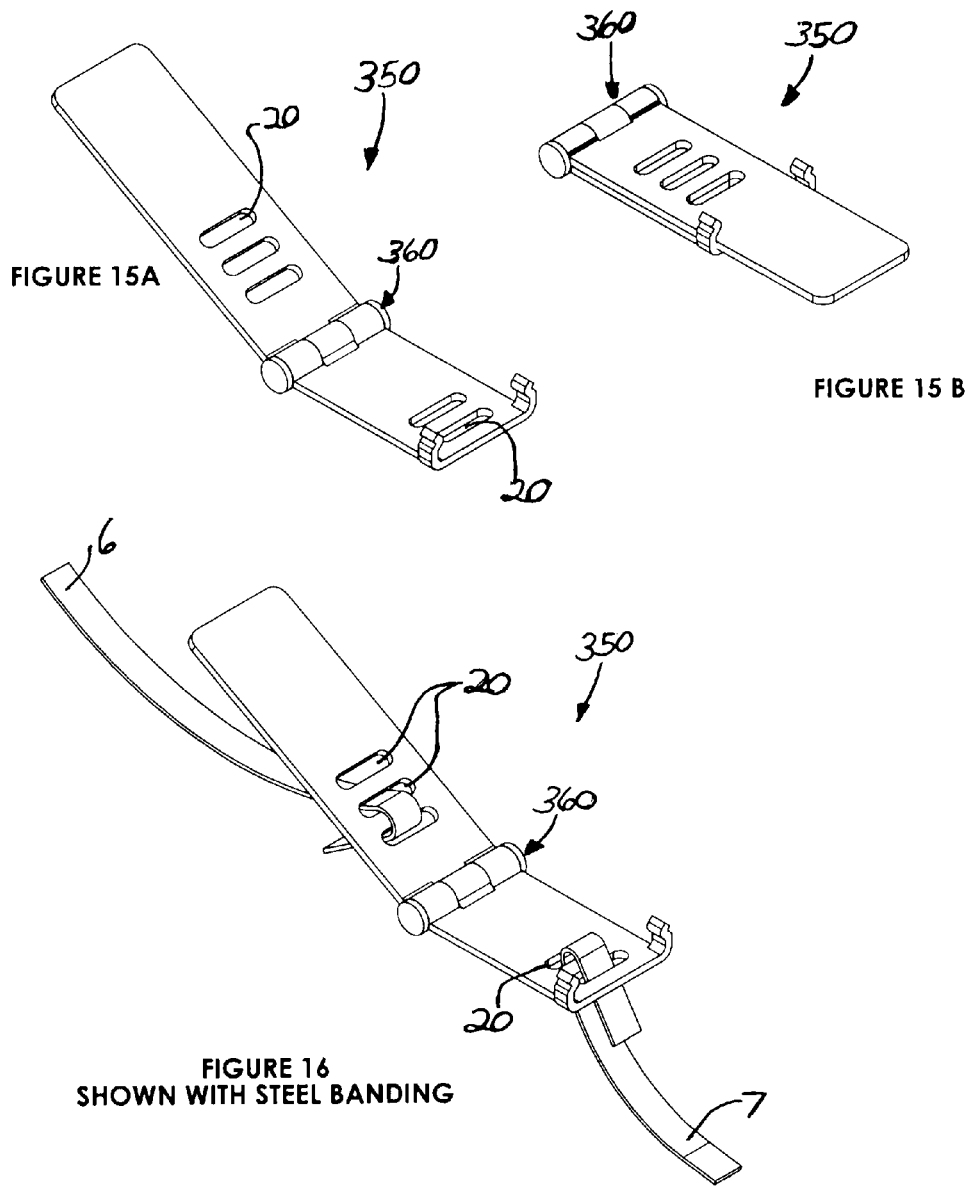

SOFT SURFACE
SELF-HOLDING BINDER

HARD SURFACE
SELF-HOLDING BINDER

HARD SURFACE
SELF-HOLDING BINDER
WITH POLY STRAPS

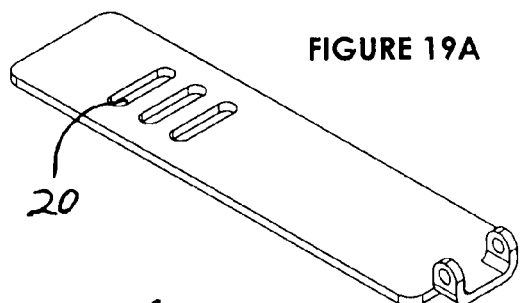
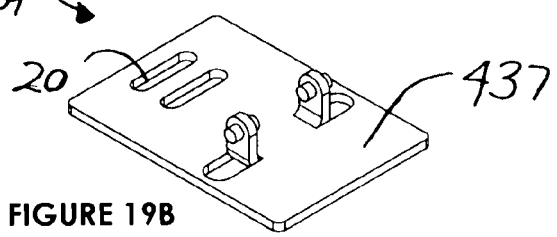
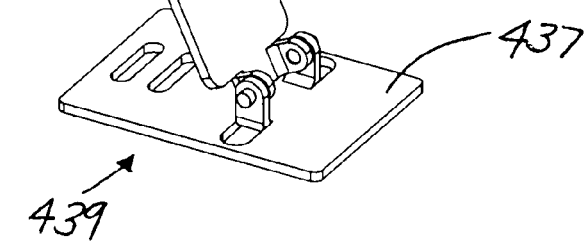
FIGURE 19A
FIGURE 19B
FIGURE 19C

POLY STRAP ISO VIEW

FLAT BINDER 1 WITH STEEL STRAPS

SHAPED ASSY WITH
CURVED BINDER AND
STEEL STRAPS

DETAIL 'A' FIGURE 28
CURVED BINDER
AND STEEL STRAPS

HINGED STRAP-BINDER

RELATED APPLICATIONS

This application claims priority benefit of U.S. Provisional Patent Application No. 61/117,825, filed Nov. 25, 2008; and is a Divisional of U.S. patent application Ser. No. 12/622,091, filed Nov. 19, 2009, now U.S. Pat. No. 8,402,887. Each aforementioned application is incorporated by reference herein.

BACKGROUND

The field of the present disclosure relates to binders used with straps and methods for using binders with straps.

Straps, such as steel banding or poly straps, are commonly used to bind items to objects, such as a lid to a crate for shipping, a water heater to a wall, goods to a pallet, and various other applications. There are various tools used to tension straps around items, for example, tensioning brackets tensioned by screws turned by a screwdriver or wrench, ratchet assemblies, and crimping tools that crimp a clip in place after another tool has been used to apply tension to the strap.

SUMMARY

Devices and methods for binding items with straps are described. In one configuration, a device for binding items with a strap is a lever that is not attached to an item to be bound and is not attached to any other object. The lever includes an axis of rotation that is proximate to an axis end of the lever, and includes a strap-retaining feature. The strap-retaining feature is used to secure a first free end of a strap proximate, that is, near, the axis end of the lever. The strap-retaining feature is also used to secure a second free end of a strap in a position where the second free end of a strap engages the lever at a point that is distal from the axis end of the lever. The lever also includes a locking device that is configured to maintain tension on a strap and to lock the lever in a closed position when the first free end of a strap and the second free end of a strap are secured to the lever and the lever is rotated from an open position to a closed position.

In one method for securing an item to an object with a strap, the strap is engaged with the object, then placed around the item. A first free end of the strap is secured to a lever so that the first free end engages proximate to an end of the lever. The lever may contact the item and/or the object, but is not attached to either. A second free end of the strap is secured to the lever so that the second free end engages the lever distal from where the first free end engages the lever. The lever is rotated from an open position to a closed position to tension the strap, and is locked in the closed position.

Additional aspects and advantages will be apparent from the following detailed description of embodiments, which proceeds with reference to the accompanying drawings.

BRIEF DESCRIPTION OF THE DRAWINGS

FIG. 1A is a top left isometric view of a lever for binding items.
FIG. 1B is a top left isometric view of a protective boot.
FIG. 1C is a top left isometric view of another lever for binding items.
FIG. 1D is a top left isometric view of another lever for binding items.
FIG. 2A is a top left isometric view of an embodiment of an extension piece.
FIG. 2B is an end view of the extension piece of FIG. 2A.
FIG. 11 is a top left isometric view of another lever for binding items.
FIG. 12A is a top left isometric view of the lever of FIG. 11 assembled with slidable blocks.
FIG. 12B is a top left isometric view of the assembly of FIG. 12A including straps retained to the lever of FIG. 11.
FIG. 15A is a top left isometric view of another lever for binding items in an open position.
FIG. 15B is a top left isometric view of the lever of FIG. 15A in a closed position.
FIG. 16 is a top left isometric view of the lever of FIG. 15A with straps retained to the lever.
FIG. 19A is a top left isometric view of another lever for binding items.
FIG. 19B is a top left isometric view of another base used with the lever of FIG. 19A.
FIG. 19C is a top left isometric view of the lever of FIG. 19A assembled with the base of FIG. 19B.

FIG. 28 is a detailed view of the lever of FIG. 27.

DETAILED DESCRIPTION OF EMBODIMENTS

Certain embodiments will now be described with reference to the drawings. The embodiments will be described in terms of a lever that is not attached to an item to be secured or bound, and is not attached to another object. But, alternate configurations may be employed with levers of different construction. Some embodiments may overcome the above noted problems associated with using current tools to tension straps, or may have other advantages.

The present inventor has recognized that using the various, commonly available tools to tension straps is expensive, bulky, and may be cumbersome. The present inventor therefore recognized a need for an improved device for tensioning straps.

Figure 27:
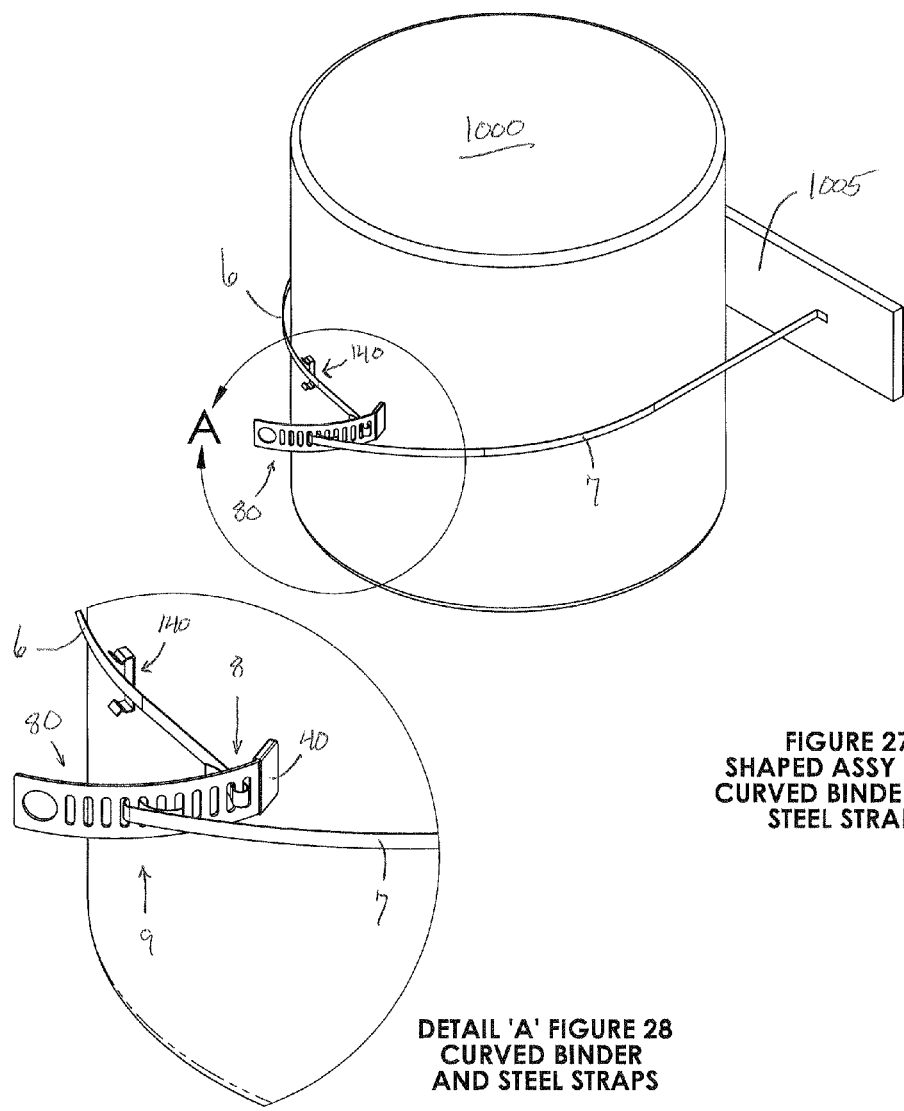
FIG. 27 is a top left isometric view of a lever used to bind an item with straps.

Referring to FIGS. 1D, 27, and 28, using an embodiment of a lever 80 (FIG. 1D) to bind an item 1000 to an object 1005 is illustrated. Generally, an object is something that an item is bound to. The lever 80 may be shaped to conform to the surface of the item 1000. A strap 6, 7 is engaged with the object 1005. Engaging a strap to an object may involve attaching or suitably securing the strap to the object, passing a strap through the object, or passing the strap around the object. For example, the object 1005 may be a wall and an end of the strap 6 and an end of the strap 7 may be attached to the wall. Alternately, the strap 6, 7 may be a single strap and may pass through holes in the wall, or otherwise be placed around the object 1005. The strap 6, 7 is passed around the item 1000 for binding the item 1000 to the object 1005.

A first free end 8 of strap 6 may be retained in apertures 95 (FIG. 1D) so that the first free end 8 is proximate the axis end 90 (FIG. 1D). A second free end 9 of strap 7 may be retained in apertures 95 so that the second free end 9 engages the lever 80 distal from the axis end 90. In accordance with the teachings set forth herein, other suitable arrangements for securing a free end of a strap to a lever may be used.

Figure 5A:
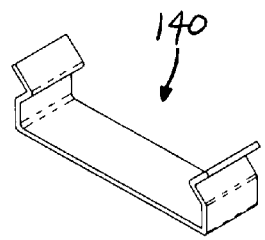
FIG. 5A is a top left isometric view of a retaining clip.

Once the first free end 8 and the second free end 9 are secured to the lever 80, the lever 80 is rotated from an open position (depicted) to a closed position, for example where both the axis end 90 and the distal end 100 of the lever 80 contact (but are not attached to) the item 1000. The lever 80 may be locked in place by the locking device 105. For example, when the distal end 100 of the lever 80 contacts the item 1000, the bent portion of the lever resulting from including the locking device 105 may act as an over-center device to lock the lever 80 in the closed position. Alternatively, or in addition to the locking device 105, a retaining clip 140 (FIG. 5A) may be located so that it is between the item 1000 and the strap 6. When the lever 80 is rotated to the closed position, the lever 80 engages the retaining clip 140, and due to the strap 6 between the retaining clip 140 and the lever 80, the retaining clip 140 locks the lever 80 in the closed position.

FIG. 1A illustrates another embodiment for a lever for binding items using straps. The lever 5 has an axis end 15, and is made from a rigid material such as steel, high strength plastic, or other suitable material. The lever 5 rotates about the rotational axis 10, which is proximate to the axis end 15 of the lever 5. In certain embodiments, the rotational axis 10 may be parallel to and tangent to the axis end 15 of the lever 5. The lever 5 is a free standing device, in other words, the lever 5 is not attached to an item that is to be bound or secured by straps, and the lever 5 is not attached to an object that an item is being bound or secured to.

Figure 23:
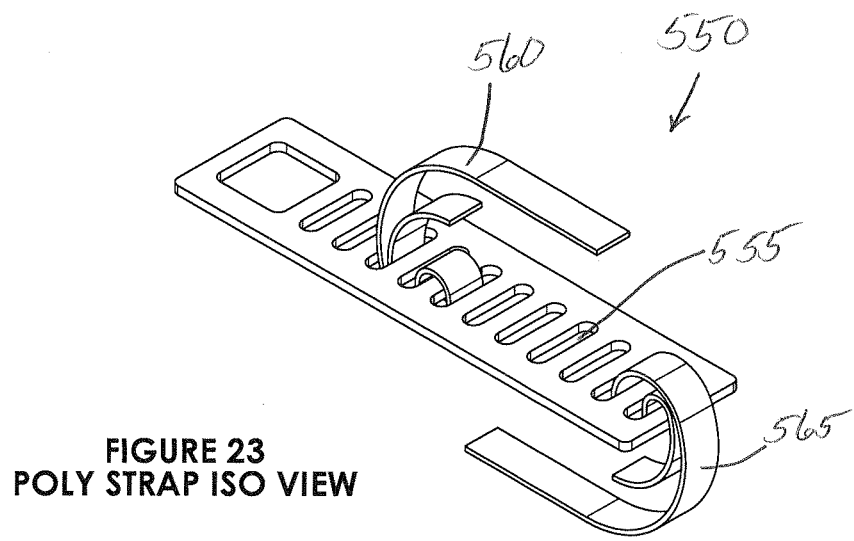
FIG. 23 is a top left isometric view of another lever for binding items with straps retained to the lever.
Figure 24:
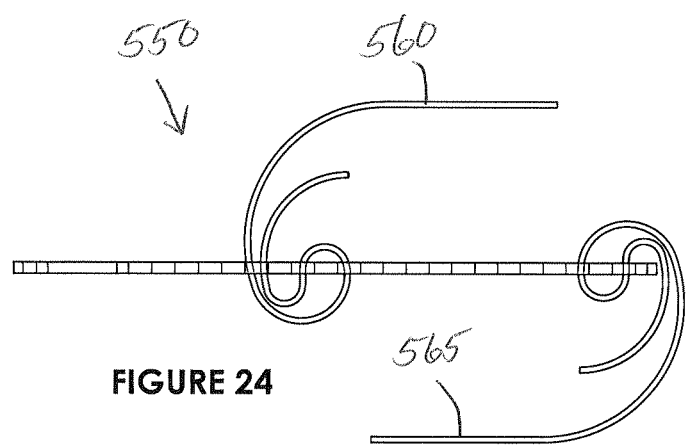
FIG. 24 is a side view of the lever of FIG. 23.
Figure 25:
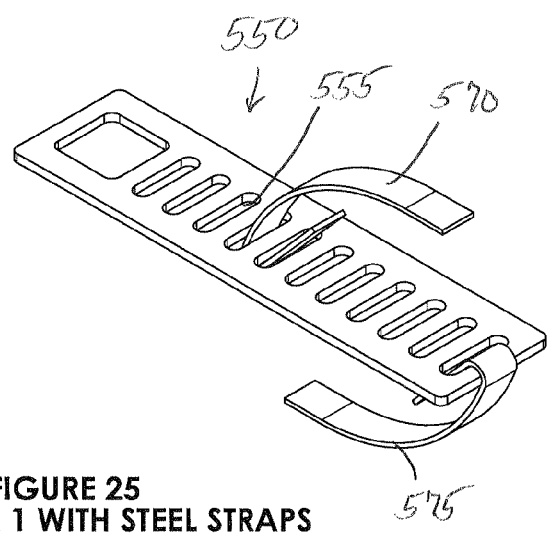
FIG. 25 is a top left isometric view of the lever of FIG. 23 with other straps retained to the lever.
Figure 26:
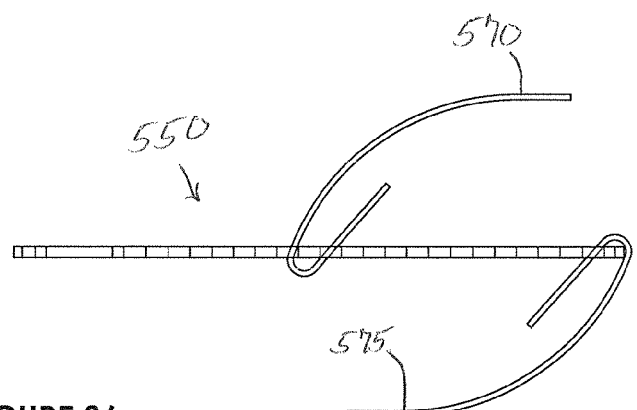
FIG. 26 is a side view of the lever of FIG. 25.

One arrangement for a strap-retaining feature is to include a plurality of apertures 20 spaced along the length of the lever 5. As illustrated in FIGS. 23-26, apertures 555 may be used to frictionally secure a first free end of a strap 560 and a second free end of a strap 565 to a lever 550. The first free end and the second free end may be ends of one strap, or may be ends of different straps. FIGS. 23 and 24 illustrate one manner for securing a strap in the plurality of apertures 555. For example, the straps 560 and 565 may be poly straps, for example, straps made from polypropylene, polyester, nylon straps, or other straps, that are relatively smooth, may readily slide over another material, or may not readily deform. FIGS. 25 and 26 illustrate an alternative manner for securing a strap in the plurality of apertures 555. For example, the straps 570 and 575 may be straps made from metal, or other suitable materials, that do not readily slide over another material, or may readily deform. When a readily deformable strap is used, such as steel banding, an end of the strap may be bent to readily fit into an aperture 555 and use the "hook" formed by the bend to assist holding the strap in place.

An alternate to securing straps directly to a lever (such as lever 45 for example) is to secure a strap 3010 to an extension piece 3000 and to secure the extension piece 3000 to a lever, such as lever 45 for example, using a tab 3005, or other suitable structure for releasably securing the extension piece 3000 to a lever. Using an extension piece 3000 may permit a user to repeatedly bind and unbind items of a similar, but slightly variable, size without requiring a user to repeatedly lace or otherwise secure a strap 3015 to the lever 45.

Figure 10A:
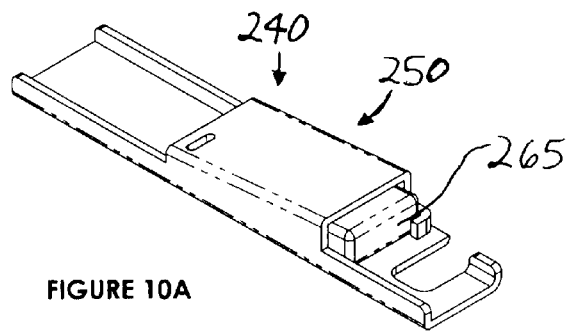
FIG. 10A is a top left isometric view of the lever of FIG. 8 assembled with the slidable block of FIG. 9A.
Figure 10B:
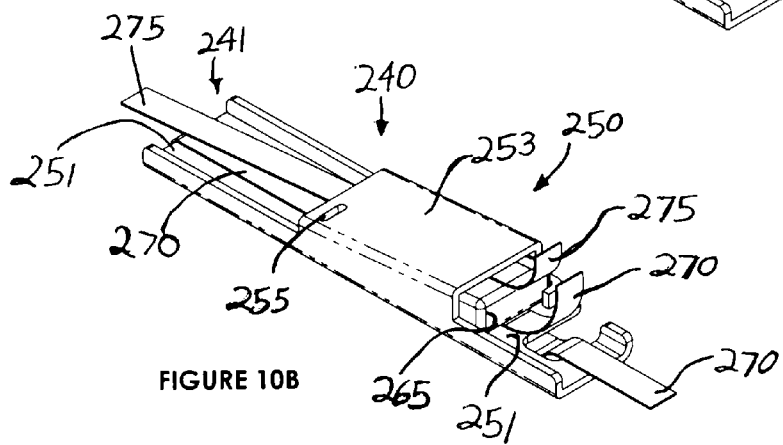
FIG. 10B is a top left isometric view of the assembly of FIG. 10A including straps retained to the lever of FIG. 8.
Figure 21A:
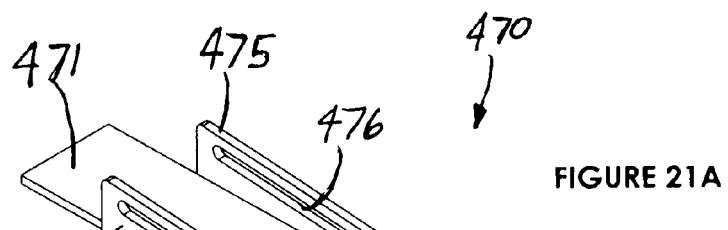
FIG. 21A is a top left isometric view of another lever for binding items.
Figure 21B:
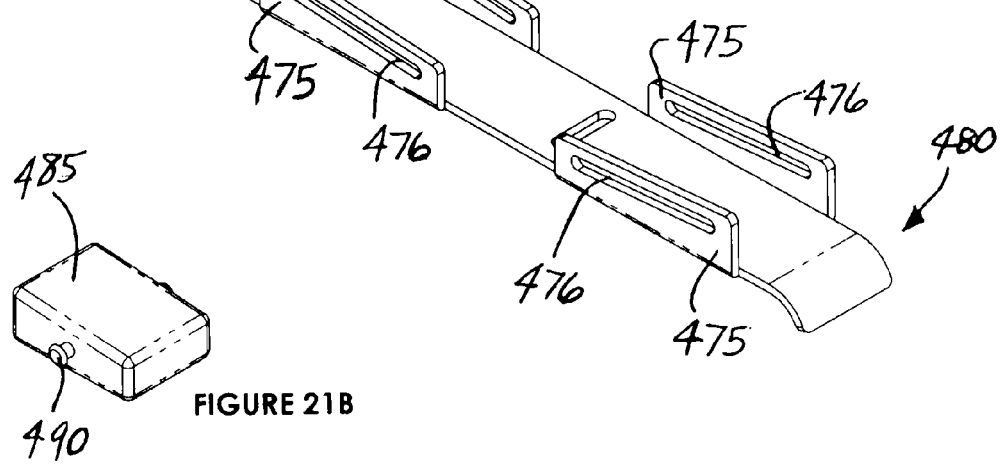
FIG. 21B is a top left isometric view of a slidable block used with the lever of FIG. 21A.
Figure 21C:
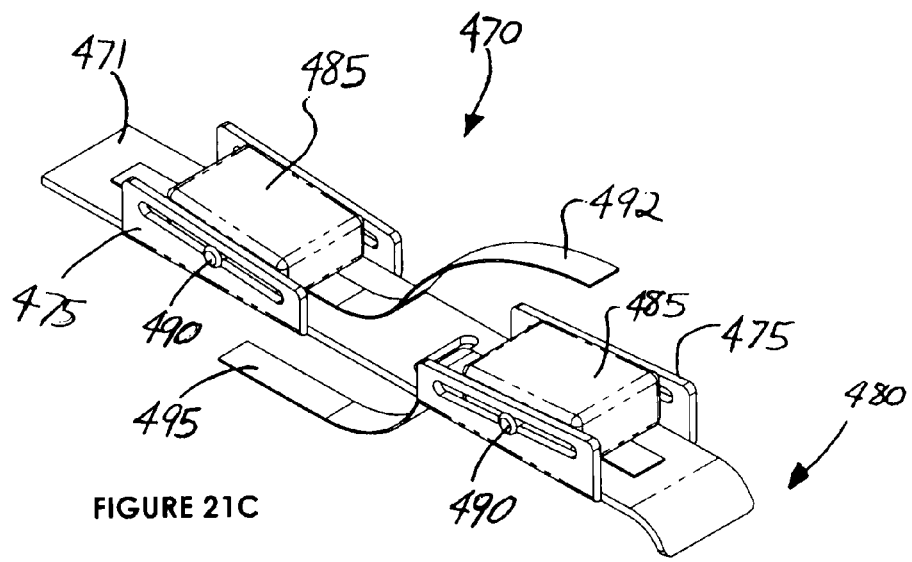
FIG. 21C is a top left isometric view of the lever of FIG. 21A assembled with two slidable blocks of FIG. 21B and with straps retained to the lever.

Other alternate arrangements for securing a second free end of a strap in a position where the second free end of a strap engages a lever distal from the axis end include those illustrated in FIGS. 10B (where strap 275 is illustrated engaging the lever 240 in the housing 250), 12B (where strap 310 is illustrated engaging the lever 280 in the housing 290), and FIG. 21C (where strap 492 is illustrated engaging lever 470 distal from the axis end 480).

Figure 8:
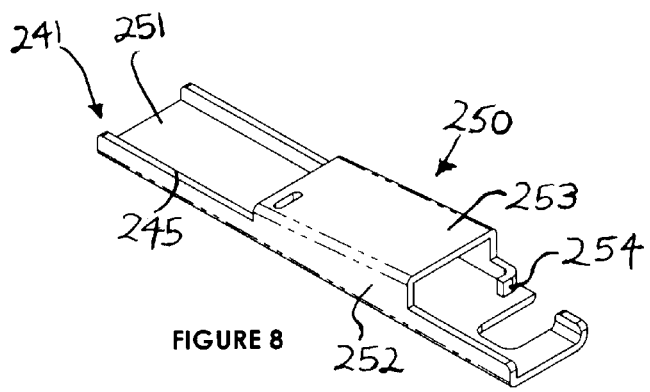
FIG. 8 is a top left isometric view of another lever for binding items.
Figure 9A:
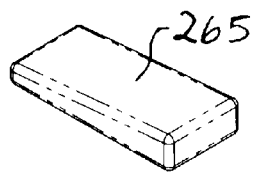
FIG. 9A is a top left isometric view of a slidable block used with the lever of FIG. 8.
Figure 9B:
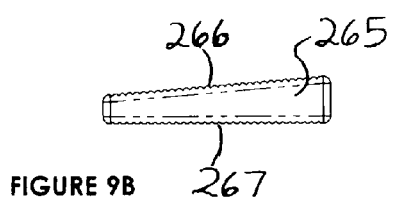
FIG. 9B is a left side view of the slidable block of FIG. 9A.

Alternate strap-retaining devices are illustrated in FIGS. 8-10B, 11-12B, and 21A-C. In FIG. 8, a lever 240 is illustrated with a housing 250. Housing 250 may include sidewalls 252, a roof 253, and a floor that includes the portion of the top surface 251 that underlies the roof 253. A slidable block 265 fits in the housing 250, and is retained to the lever 240 by arm 254. The slidable block 265 may have a rough surface 266, 267 on the top and bottom of the block 265. A first free end of strap 270 may be placed between the slidable block 265 and the floor of the housing 250 when the slidable block is in a first position. Likewise, a second free end of strap 275 is placed between the slidable block 265 and the roof 253 of the housing 250 when the slidable block is in the first position. Sliding the block 265 to a second position secures the first free end of the strap 270 and the second free end of the strap 275 in positions where the first free end of the strap 270 is secured proximate the axis end 241 and the second free end of the strap 275 is secured distal from the axis end 241. Referring to FIG. 10B, a release mechanism 255 may be included. For example, the release mechanism 255 may include a slot through the roof 253 that permits an object to be inserted through the roof 253 to move the block 265 away from the axis end 241.

Figure 13:
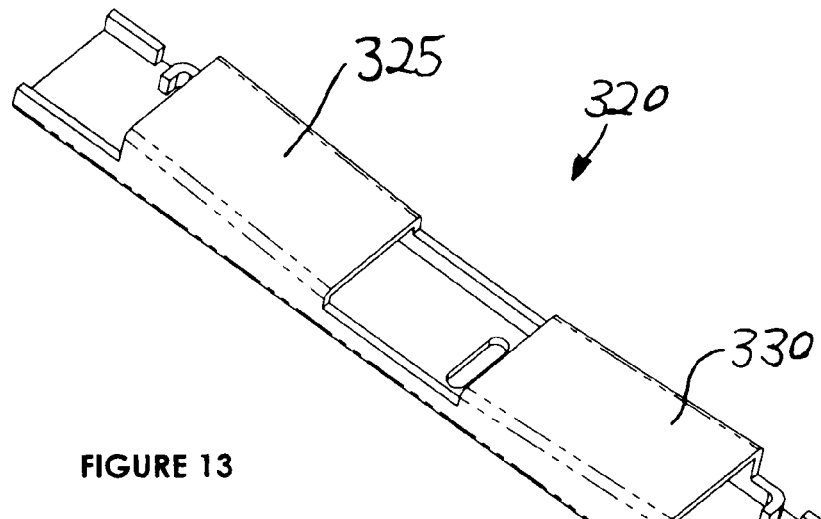
FIG. 13 is a top left isometric view of another lever for binding items.
Figure 14:
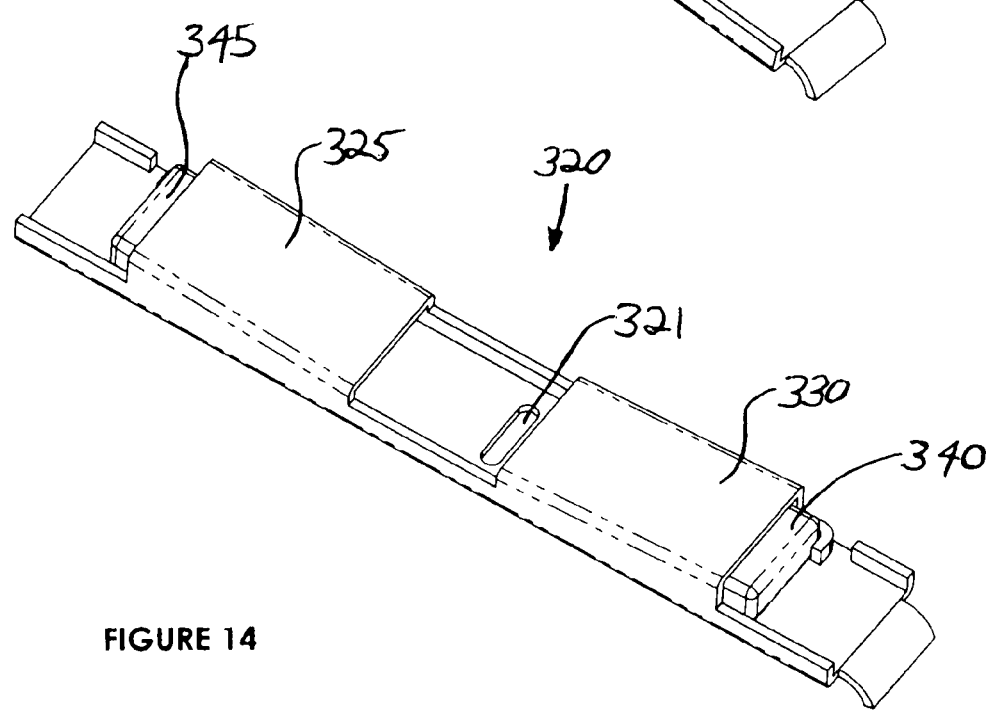
FIG. 14 is a top left isometric view of the lever of FIG. 13 assembled with slidable blocks.

Alternatively, two housings 285, 290 (FIGS. 11-12B) may be used to secure the first free end of a strap 315 proximate the axis end 281 and to secure the second free end of a strap 310 distal from the axis end 281. For example, FIGS. 13-14 show another lever 320 with two housings 325, 330 and two blocks 340, 345 that are slidable toward a centrally located aperture 321.

In FIGS. 21A-C, the housings include sidewalls 475 and the portion of the top surface 471 of the lever 470 that lies between the sidewalls 475. Slots 476 are not parallel with the top surface 471. Sliding the blocks 485, that are retained in the slots 476 by pins 490, moves the blocks 485 between a first position where straps 490 and 495 may be inserted between the blocks 485 and the top surface 471 and a second position where the straps 490 and 495 are secured between the blocks 485 and the top surface 471.

Figure 22:
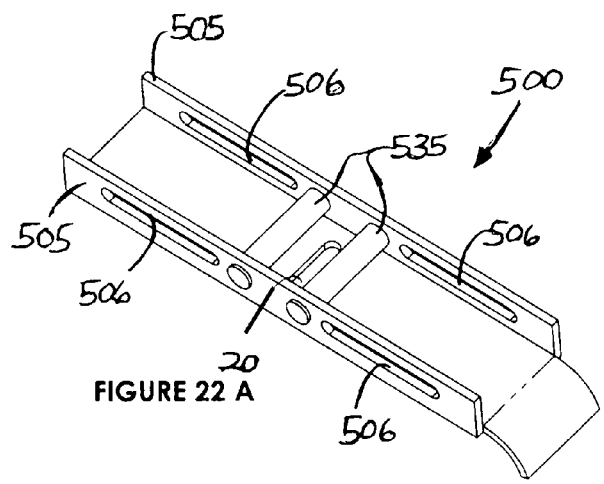
FIG. 22A is a top left isometric view of another lever for binding items.
FIG. 22B is a top left isometric view of a slidable block used with the lever of FIG. 22A.
FIG. 22C is a top left isometric view of the lever of FIG. 22A assembled with two slidable blocks of FIG. 22B.
FIG. 22D is a top left isometric view of another lever for binding items.
FIG. 22E is a top left isometric view of the lever of FIG. 22D with straps retained to the lever.
Figure 22:
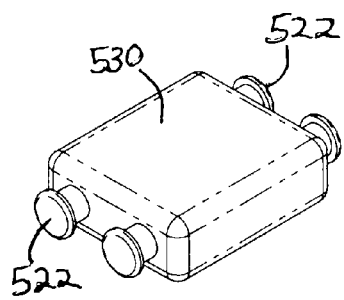
Figure 22:
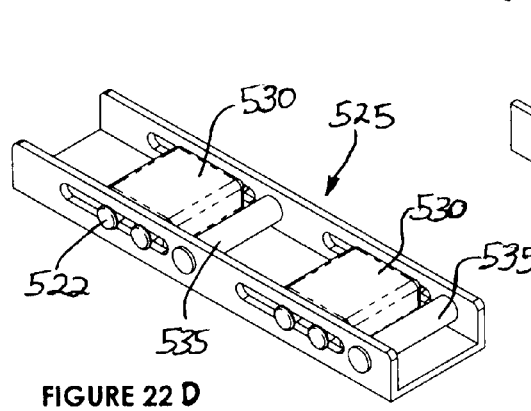
Figure 22:
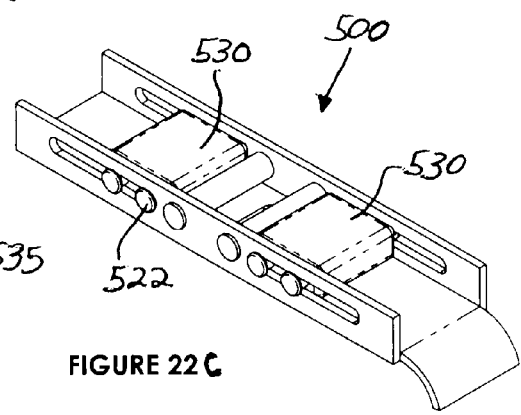
Figure 22:
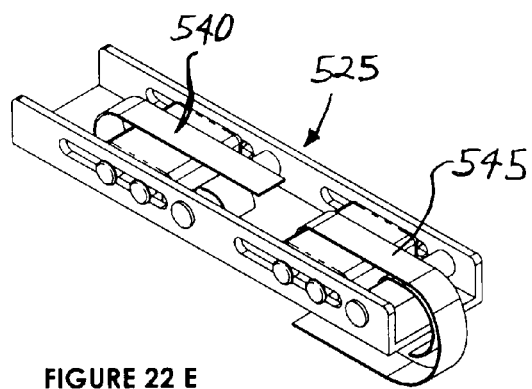

Other configurations, illustrated by lever 500 in FIGS. 22A-22C and by lever 525 in FIGS. 22D and 22E, may wrap straps 540, 545 around blocks 530 that have pins 522 to retain the blocks 530 in slots 506 of sidewalls 505. As shown in FIG. 22E, for example, the blocks 530 slide to and pinch the straps 540, 545 between the blocks 530 and pins 535 due to the force resulting from tensioning the straps 540, 545 when the lever 525 is rotated to a closed position. While the pins 535 are illustrated as being round, the pins 535 may include flat surfaces, or other shaped surfaces, and the surfaces may match the opposing surface of the block 530. Another alternate embodiment to secure a free end of a strap uses a cam or other locking mechanism to secure a strap to the lever. For example, referring to FIGS. 20A-20E, a cam device 700, 705 (or other configuration) may be retained between wings 711. The cam device 700, 705 is rotated to a first position to permit a strap 715 to be placed between the cam device 700, 705 and the upper surface 712 of the lever 710. The cam device 700, 705 is then rotated, using an actuation portion 701, 706, to a second position to lock the strap 715 in place. Another strap 720 is folded around an endmost aperture.

Figure 5B:
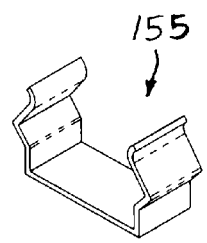
FIG. 5B is a top left isometric view of another retaining clip.

Referring to FIG. 1A, the lever 5 may also include a locking device. The lever 5 is illustrated with locking device 30, which includes a bent portion of the lever 5 near the axis end 15. The lever 5 is also illustrated with a locking aperture 35, which engages with a retaining clip, such as the retaining clip 155 illustrated in FIG. 5B, as described below.

FIG. 1B illustrates a protective boot 40 that may be placed over the axis end 15 of the lever 5 to protect the surface of an item to be bound by straps. The boot 40 may be made from a soft material such as rubber, nylon, wood, or other suitable material. A protective boot is a device or structure that operates to protect the item being bound from being marred by the lever, and may take other forms, such as plate 440 or 437, shown in FIGS. 18B and 19B, respectively.

Figure 18A:
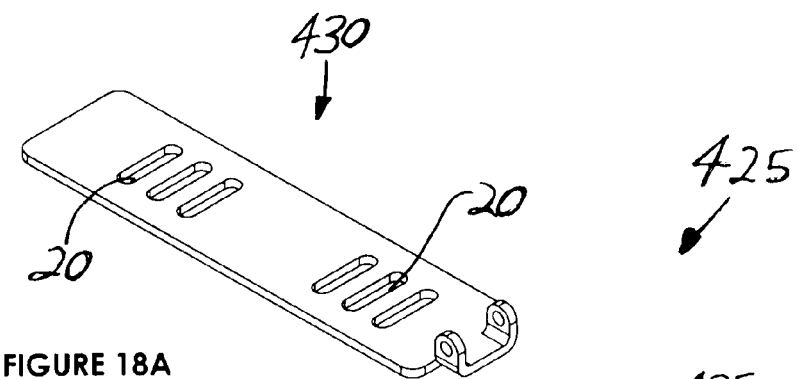
FIG. 18A is a top left isometric view of another lever for binding items.
Figure 18B:
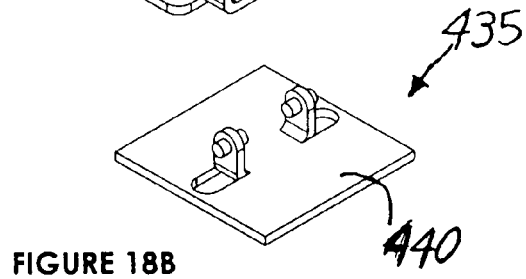
FIG. 18B is a top left isometric view of a base used with the lever of FIG. 18A.
Figure 18C:
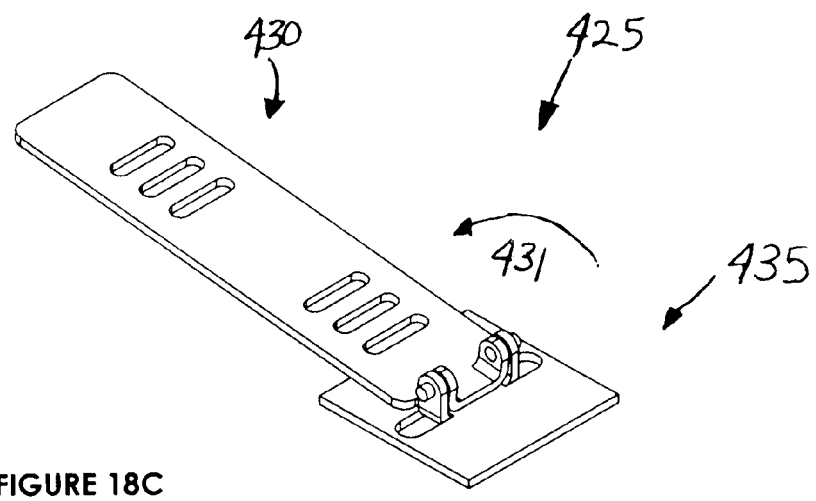
FIG. 18C is a top left isometric view of the lever of FIG. 18A assembled with the base of FIG. 18B.
Figure 20:
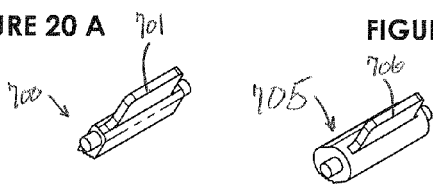
FIG. 20A is a top left isometric view of a cam device.
FIG. 20B is a top left isometric view of another cam device.
FIG. 20C is a top left isometric view of another lever for binding items.
FIG. 20D is a top left isometric view of the lever of FIG. 20C assembled with the cam device of FIG. 20A.
FIG. 20E is a top left isometric view of the assembly of FIG. 20D with straps attached.
Figure 20:
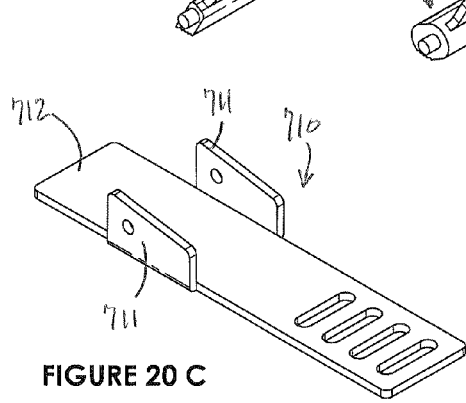
Figure 20D:
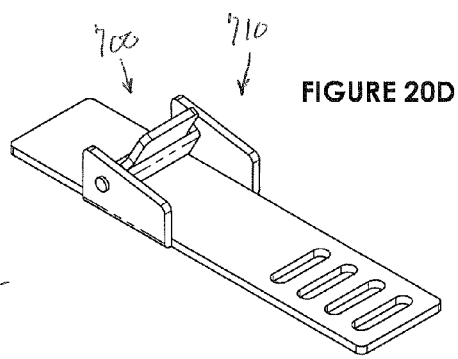
Figure 20:
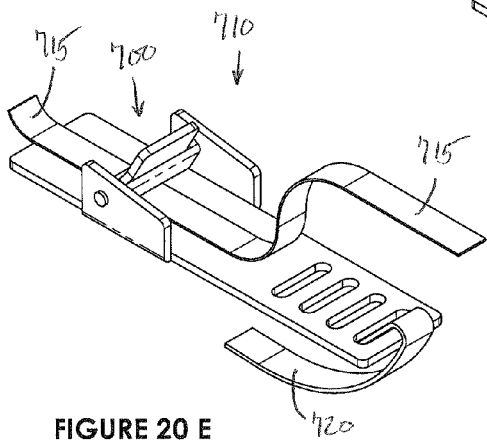

Alternate embodiments may include a hinge 360, as illustrated by a lever 350 of FIGS. 15A-16, 18A-C, and 19A-C. When the hinge 360 is used, the axis of rotation may move from being proximate to an item being bound with the strap to a location above the item being bound with the strap, as illustrated in FIGS. 18C and 19C, for example. In FIGS. 18B and 19B, the plate assembly 435, and 439, respectively, may serve to protect an item from being marred when the lever 430 or 427, respectively, is rotated to a closed position. The device 425, 426 illustrated in FIGS. 18C and 19C, respectively, may therefore include an over-center locking device that operates by rotating the lever 430 or 427 in the direction of arrow 431 or 438, respectively, to a closed position.

Figure 17A:
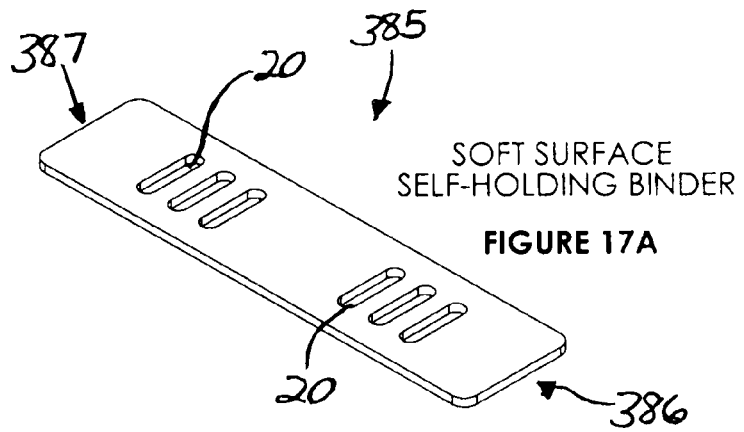
FIG. 17A is a top left isometric view of another lever for binding items.
Figure 17B:
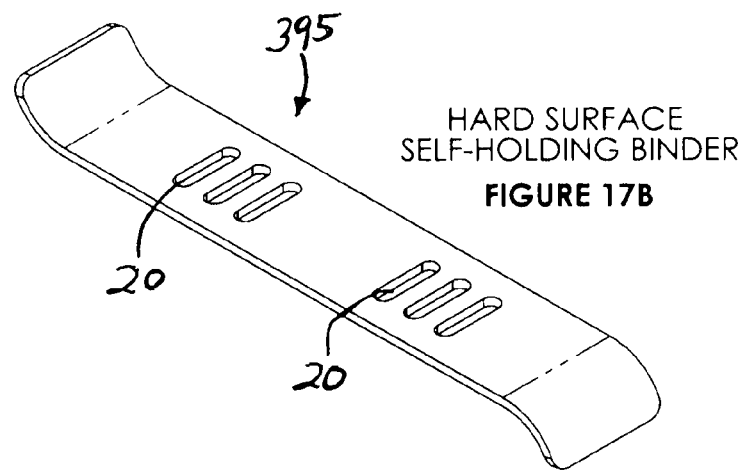
FIG. 17B is a top left isometric view of another lever for binding items.
Figure 17C:
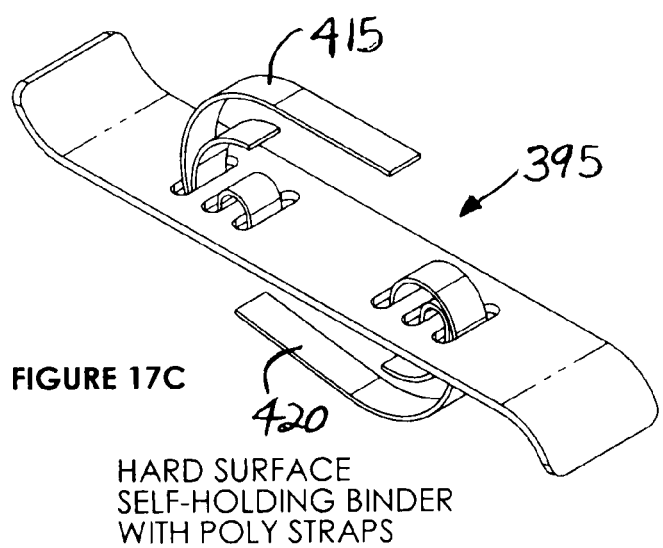
FIG. 17C is a top left isometric view of the lever of FIG. 17B with straps retained to the lever.

Another configuration, illustrated in FIG. 17A, may use a flexible material for the lever 385, such as spring steel, nylon, high density polyethylene, or other suitable material, that may permit the lever 385 to flex. Such a configuration may use one end 386 as an axis end and end 387 as a distal end. When the lever 385 is rotated to a closed position, the axis end 386 may be maneuvered so that a portion of the axis end 386 underlies the strap secured distal from axis end 386. Placing the axis end 386 under the strap that is secured distal from the axis end 386 may lock the lever 385 in place. FIGS. 17B and 17C show another lever 395 for binding items, with straps 415, 420 shown retained to the lever 395 in FIG. 17C.

Another alternative may be to use a retaining clip 155 (FIG. 5B) that engages the lever 80 using the locking aperture 110 (FIG. 1D) instead of engaging the sides of the lever 80 as the retaining clip 140 does. An alternative retaining clip 190 may engage the sides of a lever in a manner where the retaining clip 190 is not readily released from the lever.

Figure 6:
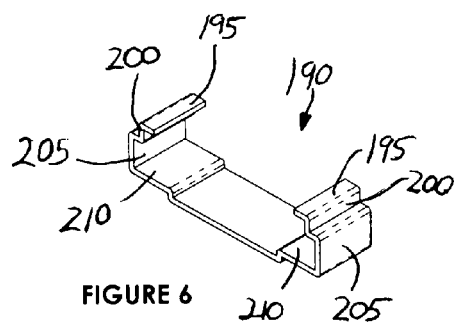
FIG. 6 is a top left isometric view of another retaining clip.

Referring to FIG. 6, for example, the retaining clip 190 may include a release feature, such as a screwdriver slot defined by walls 200, 205, and 210, where a screwdriver may be used to pry wings 195 away from one another to release the retaining clip 190 from a lever. Readily engageable and releasable clips, such as those illustrated in FIGS. 5A, 5B, and 7, may or may not include a release feature.

Figure 7:
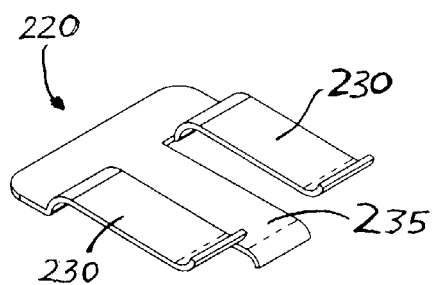
FIG. 7 is a top left isometric view of another retaining clip.

Referring to FIG. 7, for example, another alternative retaining clip 220 may engage a lever using arms 230 and 235. Arms 230 may contact one side of the lever when in the closed position and the arm 235 may contact the opposite side of the lever. A retaining clip such as the retaining clip 220 may be useful to lock a lever in a closed position when a lever does not contact an item, for example when the lever is suspended in the air because of the tension on the strap.

Figure 3A:
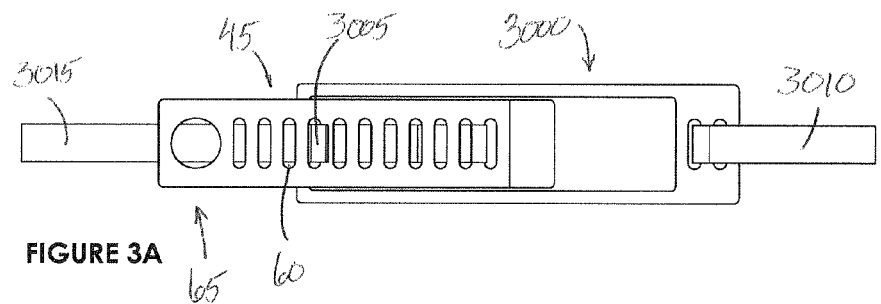
FIG. 3A is a top view of the lever of FIG. 1C used with the extension piece of FIG. 2A.
Figure 3B:
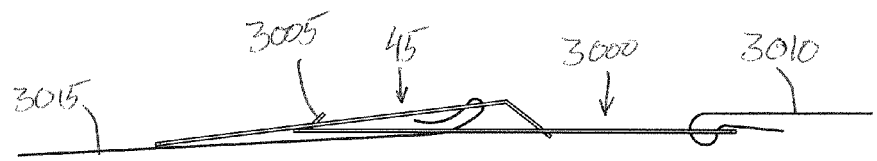
FIG. 3B is a side view of the lever of FIG. 1C used with the extension piece of FIG. 2A.
Figure 3C:
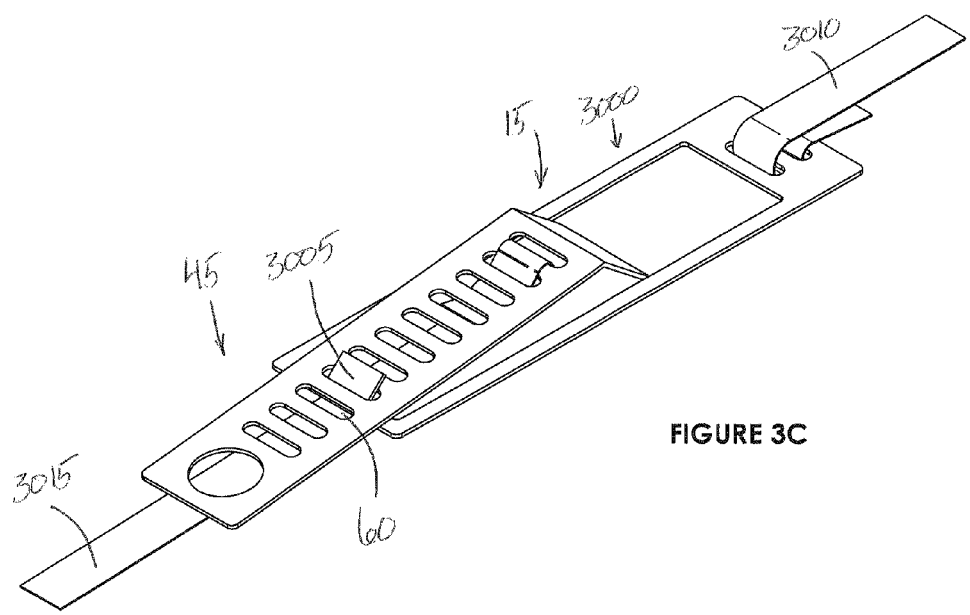
FIG. 3C is a top left isometric of the lever of FIG. 1C used with the extension piece of FIG. 2A.
Figure 4A:
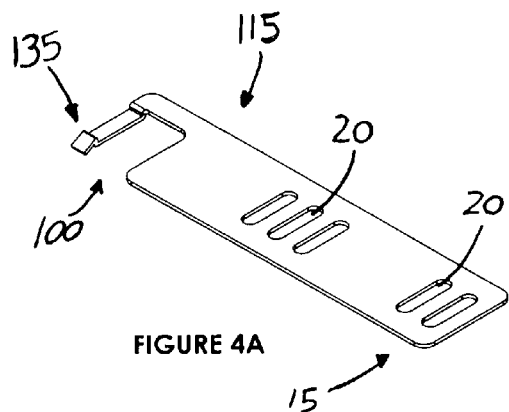
FIG. 4A is a top left isometric view of another lever for binding items.
Figure 4B:
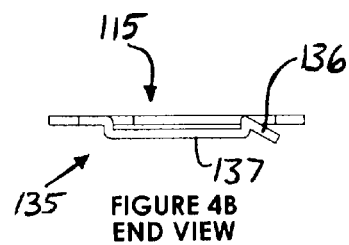
FIG. 4B is an end view of the lever of FIG. 4A.

Other configurations include a locking device, such as the locking device 135 (FIG. 4A), that is configured as a strap-engaging portion on the lever. For example, when the lever 115 is rotated to a closed position, the locking device 135 is maneuvered so that ramp portion 136 (FIG. 4B)

engages a strap (not illustrated) and used to push the strap to rest in cradle 137. Another example is illustrated in FIG. 12B where strap 315 is resting in cradle 296 of locking device 295. Note that the locking device 295 does not include a ramp, but it may in alternative configurations.

It will be obvious to those having skill in the art that many changes may be made to the details of the above-described embodiments, including, but not limited to, mixing different types of locking devices and strap-retaining features on a lever, without departing from the underlying principles of the invention. The scope of the present invention should, therefore, be determined only by the following claims.

The invention claimed is:

1. A multi-component binding-strap fastener for binding first and second free ends of, respectively, first and second straps, each of the first and second straps comprising a non-extensible, flexible strap having flat outer surfaces, the fastener comprising:
   a lever arm having upper and lower major surfaces, an axis end including a first hinge portion, a distal end, and a length along which a first strap-retaining feature is configured to secure the first free end such that it becomes tethered in a position where it engages the lever arm proximal to the distal end;
   a plate having first and second opposing surfaces, the first opposing surface including a second hinge portion that, when coupled with the first hinge portion, establishes a hinge providing an axis of rotation about which the distal end of the lever arm rotates along an operating arc of the hinge between an unclamped position that loosens tension on the first strap to a clamped position that maintains tension on the first strap as the first free end is pulled by the lever arm toward a direction of the operating arc and to an over-center height, relative to the hinge, at which the flat outer surfaces of the first free end are beneath the axis of rotation; and
   a second strap-retaining feature configured to secure the second free end such that it becomes tethered and a first confronting surface of the flat outer surfaces of the second free end is covered by the lower major surface of the lever arm as the distal end is rotated from the unclamped position to the clamped position to thereby maintain a second confronting surface of the flat outer surfaces of the first free end substantially flat against the upper major surface of the lever arm.

2. A multi-component binding-strap fastener according to claim 1, further comprising a retaining clip configured to engage the lever arm in the clamped position.

3. A multi-component binding-strap fastener according to claim 2, further comprising a release feature on the retaining clip configured to assist disengaging the retainer clip from the lever arm.

4. A multi-component binding-strap fastener according to claim 1, in which the first strap-retaining feature includes a series of apertures through the lever arm.

5. A multi-component binding-strap fastener according to claim 1, in which the first strap-retaining feature includes a housing attached to the lever arm and a slidable block retained in the housing, the housing and slidable block configured to permit the first free end to pass between the housing and the slidable block when the slidable block is in a first position and to retain the first free end in place when the slidable block is in a second position.

6. A multi-component binding-strap fastener according to claim 5, further comprising a release feature on the housing, the release feature configured to assist moving the slidable block from the second position to the first position.

7. A multi-component binding-strap fastener according to claim 1, in which the first strap-retaining feature includes a housing attached to the lever arm and a cam device retained in the housing, the cam device including an actuation portion for engaging and disengaging the cam device from the first strap.

8. A multi-component binding-strap fastener according to claim 1, further comprising a protective boot on the plate.

9. A multi-component binding-strap fastener according to claim 1, in which the second strap-retaining feature is associated with the plate.

10. A multi-component binding-strap fastener according to claim 9, in which the second strap-retaining feature is a series of apertures through the plate.

11. A multi-component binding-strap fastener according to claim 1, in which the second strap-retaining feature is associated with the lever arm.

12. A multi-component binding-strap fastener according to claim 11, in which the second strap-retaining feature is located away from the distal end and between the axis end and the first strap-retaining feature.

13. A multi-component binding-strap fastener according to claim 12, in which the second strap-retaining feature is a series of apertures through the lever arm.

14. A multi-component binding-strap fastener according to claim 11, in which the second strap-retaining feature is a series of apertures through the lever arm.

15. A multi-component binding-strap fastener according to claim 1, in which the second strap-retaining feature includes a housing attached to the plate and a slidable block retained in the housing, the housing and slidable block configured to permit the second free end to pass between the housing and the slidable block when the slidable block is in a first position and to retain the second free end in place when the slidable block is in a second position.

16. A multi-component binding-strap fastener according to claim 15, further comprising a release feature on the housing, the release feature configured to assist moving the slidable block from the second position to the first position.

17. A multi-component binding-strap fastener according to claim 1, in which the second strap-retaining feature includes a housing attached to the plate and a cam device retained in the housing, the cam device including an actuation portion for engaging and disengaging the cam device from the second strap.

18. A multi-component binding-strap fastener according to claim 1, in which the first and second straps are portions of a single strap.

* * * * *